(12) United States Patent
Fanenbruck

(10) Patent No.: US 9,095,255 B2
(45) Date of Patent: Aug. 4, 2015

(54) METHOD AND DEVICE FOR LOCATING FUNCTION-SUPPORTING TISSUE AREAS IN A TISSUE REGION

(75) Inventor: Martin Fanenbruck, Oberkochen (DE)

(73) Assignee: Carl Zeiss Meditec AG (DE)

( * ) Notice: Subject to any disclaimer, the term of this patent is extended or adjusted under 35 U.S.C. 154(b) by 515 days.

(21) Appl. No.: 12/752,609

(22) Filed: Apr. 1, 2010

(65) Prior Publication Data
US 2010/0254586 A1    Oct. 7, 2010

(30) Foreign Application Priority Data

Apr. 2, 2009   (DE) .......................... 10 2009 015 598

(51) Int. Cl.
*G06K 9/00* (2006.01)
*A61B 5/00* (2006.01)

(52) U.S. Cl.
CPC .................................... *A61B 5/0059* (2013.01)

(58) Field of Classification Search
CPC ... A61B 5/0059; G01N 21/64; G01N 21/359; G06F 3/015; G06T 7/0012
USPC ........................................................ 382/131
See application file for complete search history.

(56) References Cited

U.S. PATENT DOCUMENTS

| 5,215,095 | A | 6/1993 | Macvicar et al. | |
| 6,196,226 | B1 * | 3/2001 | Hochman et al. | 600/425 |
| 2004/0114109 | A1 * | 6/2004 | Soliz et al. | 351/221 |
| 2004/0208390 | A1 * | 10/2004 | Jiang et al. | 382/260 |

FOREIGN PATENT DOCUMENTS

DE       195 27 446 A1    10/1996

* cited by examiner

*Primary Examiner* — Hiep V Nguyen
(74) *Attorney, Agent, or Firm* — Gerald E. Hespos; Michael J. Porco; Matthew T. Hespos

(57) ABSTRACT

Functional tissue areas in a tissue region are located by illuminating the tissue by measurement illumination. Stimulation in the functional tissue areas leads to a change in at least one optical property of the reflected measurement illumination compared to the original measurement illumination. The functional tissue areas are located based on the change in the at least one optical property of the reflected measurement illumination by determining the difference between a stimulation image of the tissue region obtained during the stimulation and a comparison image of the tissue region obtained without stimulation. The difference may be formed from at least one image recorded with the measurement illumination and at least one image recorded without the measurement illumination to bring about an increase in contrast. An obtained image may be corrected on the basis of the determined topography of the tissue region to bring about an increase in contrast.

29 Claims, 5 Drawing Sheets

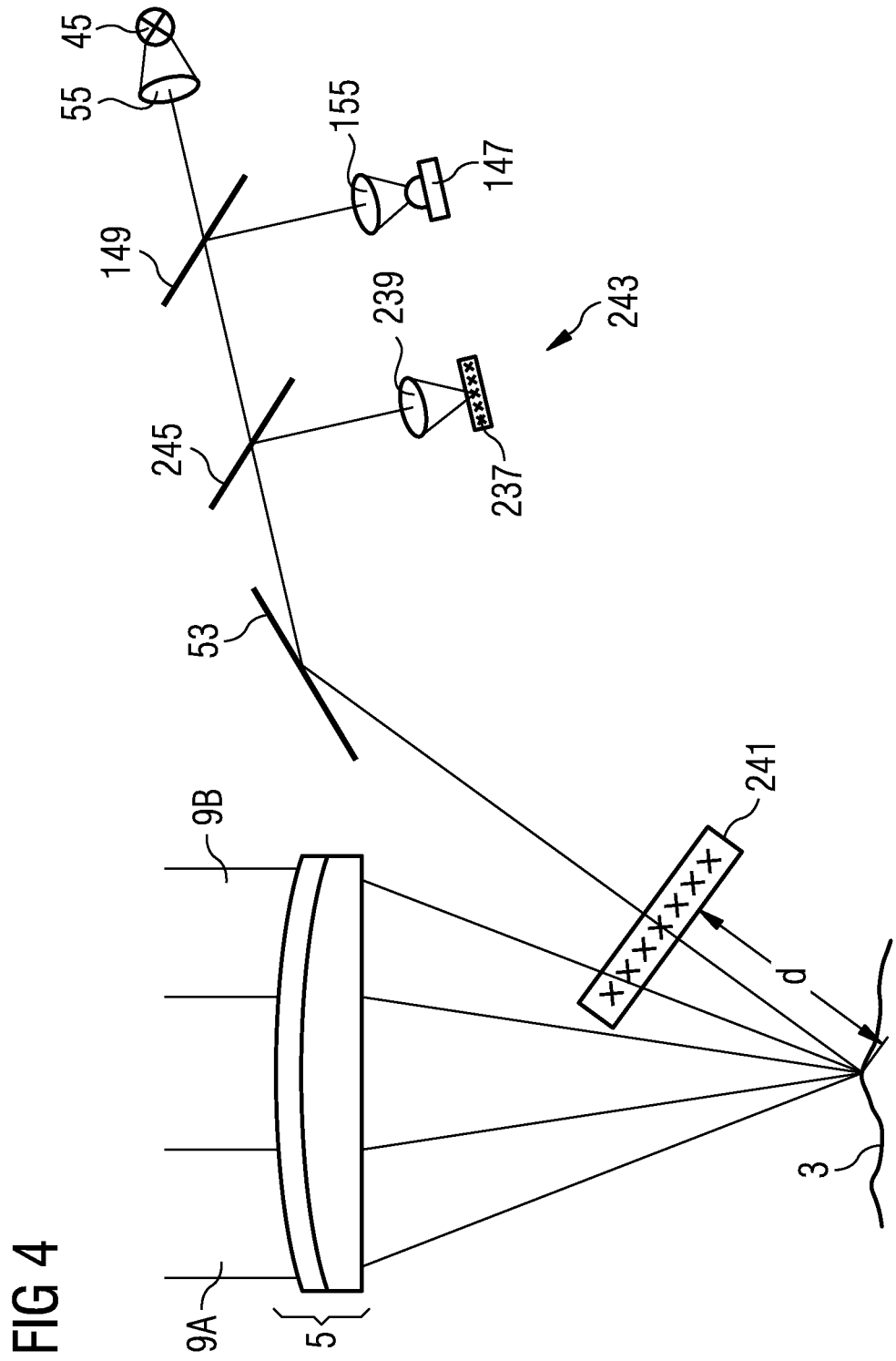

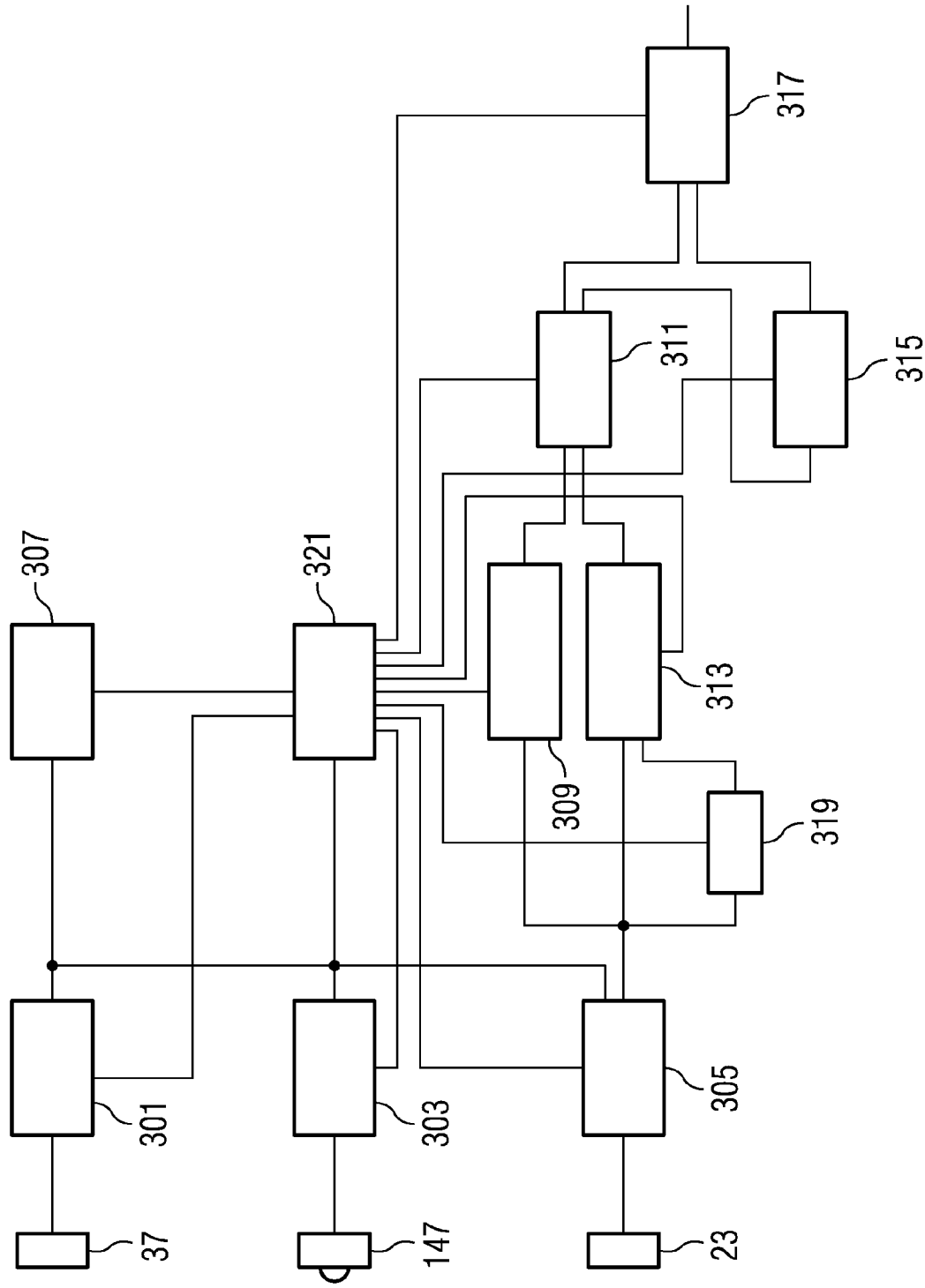

METHOD AND DEVICE FOR LOCATING FUNCTION-SUPPORTING TISSUE AREAS IN A TISSUE REGION

BACKGROUND OF THE INVENTION

1. Field of the Invention

The present invention relates to a method and device for locating functional tissue areas in a tissue region, particularly in a brain tissue region. Additionally, the invention relates to a device for carrying out the method, an operation microscope and a computer program product.

2. Description of the Related Art

In the case of tumor operations in the brain with tumors in the vicinity of eloquent brain areas, i.e. functional brain areas, for example in the vicinity of the motor cortex, in the vicinity of sensorimotor centers, in the vicinity of the speech center, etc., the treating surgeon is torn between how radical the tumor removal should be and how to sustain functional brain tissue and thus optimize the post-operative quality of life of the patient. Very precise locating of the functional tissue areas is very important in this case.

These days, typical methods for locating functional brain areas are based on electrophysiological detection of these areas, for example by means of electric stimulation of certain skeletal muscles (e.g. the calf) and measuring a potential on the surface of the brain by means of applied electrodes. Thus, this is a method involving contact. However, such methods involving contact have limitations that limit the options for application. By way of example, the minimum possible size of the electrodes and the smallest possible electrode spacing determine the resolution when locating the functional tissue areas. This cannot achieve a high-resolution display of functional tissue areas. Furthermore, a method involving contact is inevitably associated with risks resulting from contacting the tissue with an object made of tissue-extraneous material.

In order to overcome the disadvantages of the described methods involving contact, U.S. Pat. No. 6,196,226 B1 or U.S. Pat. No. 5,215,095, for example, propose imaging functional areas of the brain by means of an optical image. In the methods described in these documents, the tissue region is recorded during a stimulation leading to a change in the physiological properties of the functional areas. The change in the physiological properties in turn leads to a change in the optical properties of reflected light. Thus, the difference between a stimulation image, recorded during the stimulation, and a comparison image, recorded without stimulation, is formed in order to display the functional areas, and the functional areas are located on the basis of the difference. The option of carrying out a 3D reconstruction of a tissue region has also been disclosed, in which a difference image from a recording with stimulation and a recording without stimulation is superposed with 3D data obtained by a previously recorded MRI data record. This type of display is intended to make it easier for the medical practitioner to locate a functional region correctly.

However, it is extremely difficult to carry out the optical imaging methods described in the aforementioned documents because the changes in the reflected light connected to the functional stimulation are of low intensity. Thus, in order to obtain usable images, a multiplicity of images with and without stimulation are generally recorded in the methods described at the outset, and there is averaging over all images with stimulation and averaging over all images without stimulation before the difference image is formed. Moreover, use is generally made of expensive monochromes (CCD cameras) with a high grayscale resolution (24 bit) and relatively long integration times. Locating functional tissue areas using this takes up relatively large amounts of time, which is particularly disadvantageous if this increases the duration of the operation.

Therefore, overall, it is very difficult to generate contrast-rich images of functional regions in a short time using the described optical imaging methods.

Thus, an object of the present invention can be considered the provision of an advantageous method and an advantageous device for locating functional tissue areas in a tissue region.

Moreover, an object of the invention can be considered the provision of an advantageous operation microscope.

The provision of a computer program product, which allows an automated procedure for locating functional tissue areas, can be considered a further object.

SUMMARY OF THE INVENTION

In the method according to the invention for locating functional tissue areas in a tissue region, in particular for locating eloquent brain tissue in a tissue region of the brain, images of the tissue region are recorded with and without stimulation of the functional tissue areas. Here, the illumination of the tissue region comprises measurement illumination with at least one wavelength at which the stimulation in the functional tissue regions leads to a change in at least one optical property of the reflected measurement illumination compared to the original measurement illumination. Then, the functional tissue areas are located on the basis of the change in the at least one optical property by determining the difference between a stimulation image of the tissue region obtained during the stimulation and a comparison image of the tissue region obtained without stimulation. Herein, a multiplicity of different optical properties can be used as optical property on the basis of the change of which the functional tissue areas are located. By way of example, use can be made of, compared to the original measurement light, a change in the intensity (e.g. due to absorption changes), a change in the wavelength of the reflected measurement light, a change in the intensity distribution (e.g. due to scatter processes), a change in the polarization, etc.

When a wavelength is discussed within the scope of this description, it should be, in particular, understood as also meaning a narrow line, that is to say a narrow wavelength range extending about a central wavelength, with the measurement illumination in particular being able to comprise at least one wavelength from the ultraviolet spectral range and/or at least one wavelength from the infrared spectral range and/or at least one wavelength from the visible spectral range.

According to a first aspect of the invention, at least one image of the tissue region is recorded with measurement illumination and at least one image of the tissue region is recorded without measurement illumination, respectively with stimulation and/or without stimulation. The stimulation image of the tissue region obtained during the stimulation is then formed from the difference of at least one image recorded with the measurement illumination and at least one image recorded without the measurement illumination and/or the comparison image obtained without stimulation is formed from the difference of at least one image recorded with the measurement illumination and at least one image recorded without the measurement illumination.

As a result of the inventive recording of at least one image with measurement illumination and at least one image without measurement illumination during the stimulation (or without stimulation), information is also obtained relating to what influence the other illumination has on the image recorded with the measurement illumination, in addition to the information relating to the functional tissue areas. Thus, there generally also is background illumination while the image is recorded with the measurement light, with the background illumination allowing the medical practitioner to observe the tissue region. Moreover, scattered light from light sources not provided directly for illuminating the tissue region is also incident on the tissue region and is reflected by the latter. Forming the difference of an image recorded with measurement light during the stimulation and an image recorded without measurement light during the stimulation can eliminate or at least reduce these influences of the surroundings from the image recorded with measurement light, and this increases the contrast in the stimulation image used to locate the functional tissue areas. The elimination or reduction of the influences of the surroundings is improved as the difference between the spectral distribution of the measurement light and the surrounding light increases. Monochrome illumination or illumination with only few wavelength components is particularly suitable.

In particular, within the scope of the first aspect of the method according to the invention, the measurement illumination can be pulsed. Here, in particular, the pulses can be emitted at a frequency that cannot be resolved by the human eye and so the pulsed measurement illumination does not distract the medical practitioner. Then, in order to record the images of the tissue region, images of the tissue region are recorded during the measurement illumination pulses and between the measurement illumination pulses. This refinement offers the possibility of always being able to determine the influences of the surroundings directly before or after the recording of an image with measurement light and so quickly varying influences of the surroundings can also be taken into account. Moreover, in this refinement, the images can be recorded at a recording frequency that is an integer multiple of the pulse frequency of the measurement illumination. This eases such a synchronization of camera and measurement illumination such that in each case a recording with measurement illumination is followed by a recording without measurement illumination.

Moreover, the stimulation can also be pulsed with a stimulation pulse frequency. Typically, stimulation phases and phases without stimulation repeatedly alternate in succession, and last for approximately 30 seconds, but at least so long that the effect to be measured can be set up or the effect to be measured can decay. The dynamics of set-up and decay lie in the range of between one second and ten seconds. In order to obtain sufficient integration times, measurements are typically taken over a longer period of time. If the stimulation is pulsed, the pulse frequency of the measurement illumination is advantageously a large integer multiple of the stimulation pulse frequency. Here, the control by means of a control device preferably is such that the same number of images is respectively recorded during a stimulation phase and during a phase without stimulation.

Within the scope of the first aspect of the method according to the invention, in addition to the measurement illumination, there can also be continuous illumination of the tissue region by broadband light, for example as background illumination for a treating medical practitioner. The images of the tissue region without measurement illumination are then recorded with the continuous illumination of the tissue region. This refinement of the method allows the use of a filter for generating the measurement illumination, in particular for generating measurement illumination pulses, which filter filters the at least one wavelength of the measurement illumination out of the broadband illumination light. The filter is inserted into the illumination beam path whenever there should be no measurement illumination. In other words, the wavelength used as measurement illumination or the wavelengths used as measurement illumination is or are routinely filtered out of the broadband illumination. The filter is only removed if there should be measurement illumination and so the broadband illumination now also comprises the measurement illumination with the corresponding wavelength or the corresponding wavelengths. Filters for filtering out the broadband illumination in the observation beam path (leading to the recording apparatus) can then be dispensed with because the effects of the broadband illumination can be subtracted by forming the difference.

If the measurement illumination is pulsed, the filter can for example be arranged on a filter wheel or an oscillating support, which is introduced into the illuminated beam path during part of the period of the oscillation. Linear paths in particular can be considered as paths along which the oscillation takes place, without this precluding an oscillation along a curved path.

An alternative option for generating the measurement illumination consists of using a measurement light source emitting with the at least one wavelength of the measurement illumination in addition to the continuous illumination, which measurement light source can be connected during the measuring procedure. This refinement can also dispense with a filter in the observation beam path because the effects of the broadband illumination can be subtracted by forming the difference.

In a development of the first aspect of the method according to the invention, the measurement illumination comprises a first wavelength, at which the stimulation in the functional tissue areas leads to a change in at least one optical property of the reflected measurement illumination, and at least one second wavelength, at which the stimulation in the functional tissue areas leads to a change in at least one optical property of the reflected measurement illumination. This affords the possibility of using images of different wavelengths for locating the functional tissue areas, which can be advantageous, particularly in view of characterizing the functional areas. The measurement illumination with the first wavelength and the second wavelength can in this case be brought about either simultaneously or in succession. Successive illumination by both wavelengths is possible in particular when the measurement illumination is brought about by means of measurement illumination pulses. Then, for example, there can be the following pulse succession: measurement pulse 1, measurement pulse 2, pause pulse, in which there is no measurement illumination, measurement pulse 1, measurement pulse 2, pause pulse . . . .

According to a second aspect of the method according to the invention, the topography of the tissue region is determined. An image obtained during the stimulation or an image obtained without stimulation is corrected in respect of the topography of the tissue region on the basis of the determined topography data before the difference between the stimulation image of the tissue region, obtained during the stimulation, and a comparison image of the tissue region, obtained without stimulation, is determined.

The second aspect of the method according to the invention is based on the recognition that a spectroscopic examination, that is to say for example the determination of differences between reflected measurement light and original measurement light, can in principle also be undertaken using reflection measurements, but, in doing so, problems always occur when the sample to be examined does not have a defined planar surface. This is because, depending on the angle of incidence of the illumination light, there are undefined radiation and scatter angles during the reflection, which make it drastically more difficult to make a statement about the actual intensity of the light reflected by one point of the tissue region. In the case of objects without a defined planar surface, which tissue regions without special preparation typically are, the aforementioned undefined radiation and scatter angles lead to a reduction in the contrast when detecting changes in the reflected measurement light compared to the original, non-reflected measurement light. In the second aspect of the invention, the contrast is now increased by virtue of the fact that the image recorded with measurement light is corrected in respect of the topography of the recorded tissue region. Here, the correction can be undertaken before generating the stimulation image or on the stimulation image itself after the stimulation image has been created.

For the purpose of increasing the contrast, the second aspect of the method according to the invention can be used on its own, but in particular also in conjunction with the first aspect of the method according to the invention, that is to say together with an increase in contrast by forming the difference between an image recorded during the stimulation with measurement illumination and an image recorded during the stimulation without measurement illumination. Since both aspects lead to an increase in contrast, the combination of the two aspects enables a particularly good contrast ratio in the stimulation image.

The topography of the tissue region can be determined by evaluating a distortion present in the recorded images of a pattern reflected by the tissue region. In the process, the pattern does not have to be a real pattern, but can for example be an air image of a striped illumination in the object space. A so-called deflectometric method of this kind can be used to determine the local incline of the tissue at a measurement point, and the determined incline can be used to determine the radiation angle and the scatter angle. Knowledge of this can correct the intensity emitted by the corresponding point such that effects of the surface topography can be subtracted from the image obtained by the reflected measurement light. In the process, the illumination used to generate the pattern in principle can be the measurement illumination itself, but can also be light not originating from the measurement illumination.

Here, reference is made to the fact that when determining the topography is discussed within the scope of the invention, this should not necessarily be understood as meaning that the global topography of the tissue region is determined. It is entirely sufficient to determine the local topography of a measurement point, which can basically be specified by its incline with respect to a reference plane, without ever producing a topographic map of the tissue region. Nevertheless, the generation of a topographic map can be advantageous, for example for generating a three-dimensional display of the tissue region. Determining the local angle of the incline within the scope of a deflectometric method is described in, for example, US 2008/0317334 A1. Reference is made to the disclosure of this document in respect of determining the incline angle at a measurement point.

The surface of the tissue region, e.g. the surface of the brain, typically has more or less the same moisture everywhere and it is kept moist by drizzling on saline solution. Disturbing reflections caused by total reflection can occur on this film of moisture, wherein the occurrence of total reflection depends on the local incline of the tissue region. According to a development of the second aspect of the method according to the invention, the topography data can be used to determine those regions in the tissue region in which total reflection can be expected. Masking regions of total reflection thus can lead to a further increase in contrast. By way of example, when recording the images, the sensitivity of the recording can be reduced for this in those zones of the tissue region in which the moisture leads to total reflection. Then there can still be a determination according to the invention of the functional tissue areas with still usable measurement results at the locations without total reflection. By contrast, at the locations with total reflection, all the incident measurement light would be reflected directly by the film of moisture and so the reflected light carries no information relating to the tissue lying therebelow and can thus be dispensed with out any repercussions.

As an alternative to determining the topography of the tissue region by means of deflectometric methods, use can also be made of the topography by means of pattern-projection methods, in which a pattern such as a stripe pattern is directly projected onto the tissue region and the topography is determined from the image of the pattern; a triangulation method; a photogrammetric method; a shape-shading method or a time-of-flight method. In principle, a person skilled in the art knows the methods and so they are not explained in any more detail here.

Moreover, according to the invention, provision is made for a device for carrying out the method according to the invention. Such a device for locating functional tissue areas in a tissue region comprises:

a measurement illumination device for generating measurement illumination comprising at least one wavelength at which stimulation of the functional tissue areas leads to at least one change in at least one optical property of the reflected measurement illumination in these tissue areas,
  an electronic image sensor for recording images of the tissue region,
  an evaluation unit for locating the functional tissue areas by determining a difference between a stimulation image of the tissue region obtained during the stimulation and a comparison image of the tissue region obtained without stimulation.

According to the first aspect of the invention, a control apparatus is connected to the electronic image sensor, which control apparatus controls the electronic image sensor such that, during the stimulation and/or without stimulation, it records images of the tissue region with the measurement illumination and images without the measurement illumination. Furthermore, a difference image generator is connected to the electronic image sensor for receiving the images. The difference image generator determines a difference image from at least one image recorded with the measurement illumination during the stimulation and at least one image recorded without the measurement illumination during the stimulation and/or a difference image from at least one image recorded with the measurement illumination but without stimulation and at least one image recorded without the measurement illumination and without stimulation, and outputs the difference image to the evaluation unit. The latter is connected to the difference image generator for receiving a difference image obtained with stimulation from the stimulation image obtained during the stimulation and/or a difference image obtained without stimulation from the comparison image.

The device according to the invention as per the first aspect of the invention affords the possibility of carrying out the method according to the invention as per the first aspect of the invention and therefore has the properties and advantages already described with reference to the first aspect of the method.

The measurement illumination device can in particular be designed to generate a pulsed measurement illumination. The control apparatus connected to the electronic image sensor then controls the image sensor such that it records images of the tissue region during the measurement illumination pulses and records images between the measurement illumination pulses. In this refinement, there can be, in particular, a synchronization of the pulse rate of the measurement illumination device and the recording rate of the image sensor such that, in the case of two successive recordings, one is in each case recorded with measurement light and one is recorded without measurement light.

In order for example to allow background illumination during the measurement, the device according to the invention can in particular have an illumination device for the continuous illumination of the tissue region with broadband illumination light. In such a refinement, the measurement illumination device can in particular also be integrated into the illumination device for continuous illumination if there is a filter that can be brought into the illumination beam path of the illumination device and that filters out the at least one wavelength of the measurement illumination from the broadband illumination light. As was already described with reference to the method, such a filter would not be inserted into the illumination beam path when there should be illumination by the measurement light. If there should be pulsed illumination by the measurement light, the filter can in particular be arranged on a filter wheel or an oscillating support. By setting a constant oscillation frequency, such a refinement allows the generation of a constant pulse frequency. Moreover, the pulse frequency can easily be set in such a refinement as well by setting the oscillation frequency or the rotational frequency.

However, the measurement illumination device can also be present in addition to the illumination device for the continuous illumination, and can be connected to the latter. This refinement allows the targeted matching of a light source generating the measurement light to the generation of the at least one wavelength at which a stimulation of the functional tissue areas leads to at least one change in at least one optical property of the reflected measurement illumination in said areas. Moreover, a loss of intensity as a result of the filter and/or an influence on the color of the broadband illumination by a filter can be avoided.

In a development of the device as per the first aspect of the invention, the measurement illumination device has a first wavelength, at which the stimulation in the functional tissue areas leads to a change in the at least one optical property of the reflected measurement illumination, and at least one second wavelength, at which the stimulation in the functional tissue areas leads to a change in the at least one optical property of the reflected measurement illumination. Herein the measurement illumination apparatus can in particular be associated with a measurement illumination control apparatus, which allows a pulsed operation of the measurement illumination device such that measurement illumination pulses at the first wavelength and measurement illumination pulses at the second wavelength are emitted in succession. This affords the possibility of detecting the change in each wavelength range independently of the change in the other wavelength range which prevents the wavelength ranges from exerting a negative influence on one another during the measurement. The measurement at a plurality of wavelengths may if appropriate allow a more precise display of the functional tissue areas in the generated image.

As per the second aspect of the invention, the device according to the invention comprises a topography acquisition unit, which determines topography data of the tissue region. It furthermore comprises a correction unit, which is connected to the electronic image sensor for receiving the images and to the topography acquisition unit for receiving the topography data. The correction unit is designed to determine, from an image recorded during the stimulation, an image corrected on the basis of the determined topography data. The correction unit is connected to the evaluation unit for outputting the corrected image from the stimulation image obtained during the stimulation. The device according to the invention as per the second aspect of the invention can be used independently of the first aspect of the invention or can be combined with a device designed as per the first aspect of the invention. The combination of devices as per the first aspect of the invention and as per the second aspect of the invention in particular allows the generation of particularly contrast-rich stimulation images. In the process, the correction can already be undertaken on the images recorded with the measurement light. Alternatively, it is also possible for the correction to be undertaken only on a difference image that was obtained from an image recorded with measurement light and an image recorded without measurement light.

The properties and advantages that can be obtained with the device according to the invention as per the second aspect of the invention correspond to those that were already described with reference to the second aspect of the method according to the invention. Thus, they are not described again at this point.

In particular, the topography unit can comprise a pattern-projection unit, a triangulation unit, a photogrammetric unit, a shape-shading unit or a time-of-flight unit. However, alternatively it is also possible for the topography acquisition unit to comprise a pattern generator for generating a pattern to be reflected by the tissue region and a deflectometry unit for determining the topography data from the reflected pattern.

In the device according to the invention as per the second aspect of the invention, there can in particular also be a total-reflection determination unit integrated in or connected to the topography acquisition unit for receiving the topography data. This total-reflection determination unit is then designed to determine those zones of the tissue region in which total reflection occurs due to a film of moisture present on the tissue region on the basis of the topography data, and output corresponding total-reflection data.

Furthermore, in this refinement, there can be an adjustment apparatus connected to the electronic image sensor for acting on the light sensitivity thereof and to the total-reflection determination unit for receiving the total-reflection data. This adjustment apparatus is designed to reduce the light sensitivity of the electronic image sensor in pixel areas, in which tissue region sections with total reflection are imaged, in particular below the saturation limit, when recording the images recorded with the measurement illumination. This affords the possibility of masking tissue region sections with total reflection from the recording of the stimulation image. In general, a useable measurement result then can still be obtained for the remaining, unmasked regions.

Within the scope of the invention, the units used to increase the contrast in the stimulation image in principle can also be used to increase the contrast in the comparison image.

The device according to the invention can in particular be integrated in an operation microscope.

A computer program product according to the invention has computer readable program means for executing, on a computer, the steps of the method according to the invention as per the first aspect of the invention and/or of the method according to the invention as per the second aspect of the invention. This allows the corresponding method to be carried out automatically.

BRIEF DESCRIPTION OF THE DRAWINGS

Further features, properties and advantages of the present invention emerge from the following description of exemplary embodiments with reference to the attached figures.

FIG. 4 shows a fourth exemplary embodiment of the device according to the invention.

FIG. 5 shows the device according to the invention for locating functional tissue areas in the form of a functional block diagram.

DETAILED DESCRIPTION OF THE PREFERRED EMBODIMENTS

In the following text, the basic design of a device according to the invention for locating functional tissue areas in a tissue region will be explained with reference to FIGS. 1 to 4 using the example of an operation microscope into which the device according to the invention is integrated.

Figure 1:
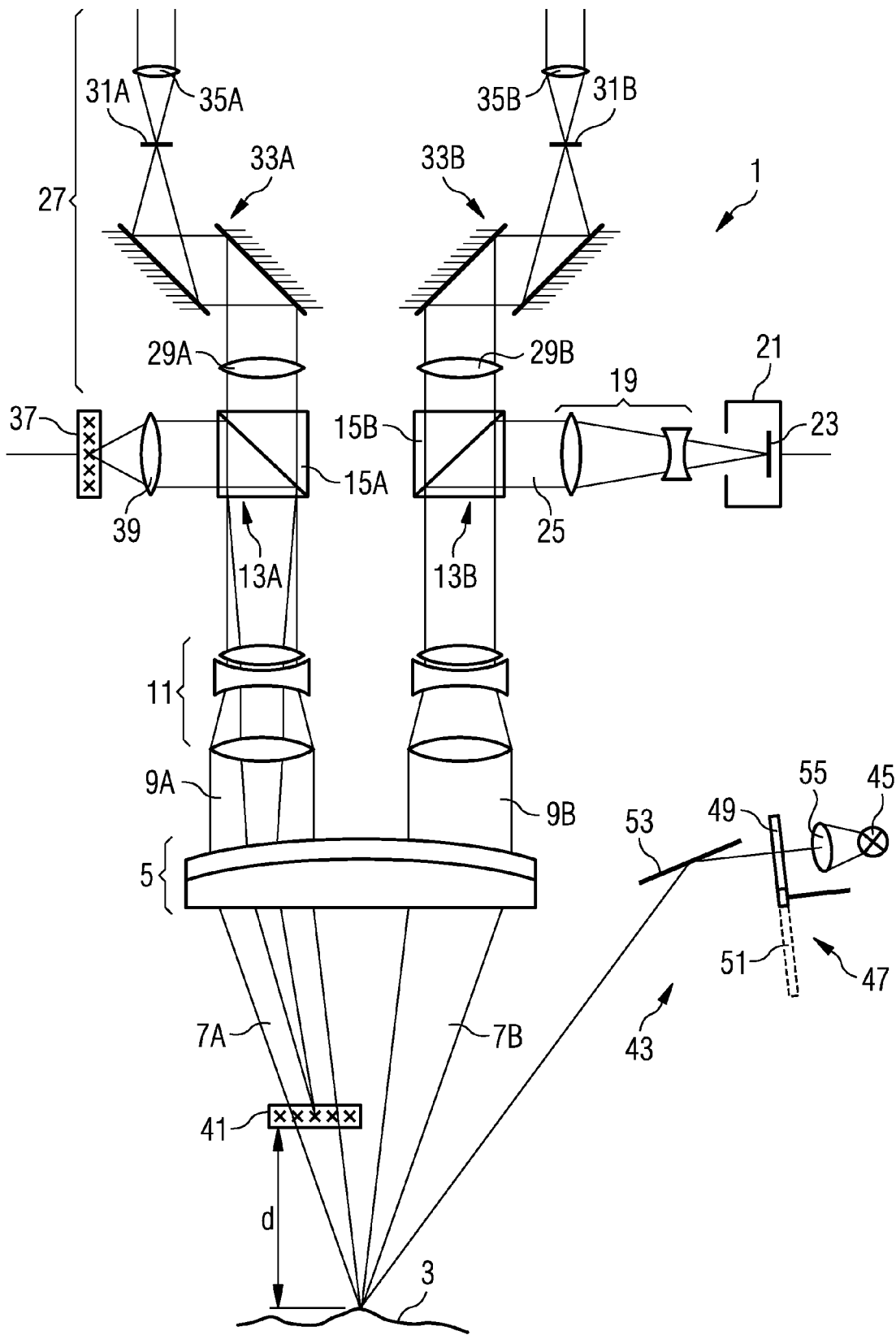
FIG. 1 shows an operation microscope with a first exemplary embodiment of the device according to the invention for locating functional tissue areas.

The operation microscope 1 shown in FIG. 1 comprises as essential components an objective 5, which should be made to face an observation object 3 and, in the present exemplary embodiment, is illustrated as an achromatic lens designed from two mutually cemented partial lenses. The observation object 3, namely the tissue region whose functional tissue areas are intended to be located, is arranged in the focal plane of the objective 5 such that the tissue region 3 is focused at infinity, that is to say a divergent bundle of rays 7 emanating from the tissue region 3 is converted into a parallel bundle of rays 9 when passing through the objective 5.

Instead of using only one achromatic lens, as is used as an objective 5 in the present exemplary embodiment, it is also possible to use an objective lens system made up of a plurality of individual lenses, for example a so-called varifocal lens system, which allows a variation in the working distance of the operation microscope 1, i.e. the distance of the focal plane from the objective 5. The tissue region 3 arranged in the focal plane is also focused at infinity in such a varifocal system, and so there is also a parallel bundle of rays on the observer side in the case of a varifocal lens system.

A magnification changer 11 is arranged on the observer side of the objective 5 and it can be designed either as a zoom system for a continuous change of the magnification factor, like in the illustrated exemplary embodiment, or as a so-called Galilean changer for stepped change of the magnification factor. In the case of a zoom system, which is generally designed as a lens combination with three lenses, the two object-side lenses can be displaced for varying the magnification factor. By contrast, in a Galilean changer, there are a plurality of fixed lens combinations that represent different magnification factors and that can be alternately inserted into the beam path. Both a zoom system and a Galilean changer convert an object-side parallel bundle of rays into an observer-side parallel bundle of rays with a different bundle diameter. Here, the magnification changer 11 is already part of the binocular beam path of the operation microscope 1, i.e. it has a separate lens combination for each stereoscopic partial beam path 9A, 9B of the operation microscope 1.

On the observer side, the magnification changer 11 is adjoined by an interface arrangement 13A, 13B, which can be used to connect external equipment to the operation microscope 1 and which in the present exemplary embodiment comprises beam-splitter prisms 15A, 15B. However, in principle, different types of beam splitters can also be used, for example partly transparent mirrors. In the present exemplary embodiment, the interfaces 13A, 13B are used for coupling a bundle of rays out of the operation microscope 1 (beam-splitter prism 15B) and for coupling a bundle of rays into one of the partial beam paths of the operation microscope 1 (beam-splitter prism 15A).

In the present exemplary embodiment, the beam-splitter prism 15A in the partial beam path 9A serves for mirroring into the partial beam path 9A of the operation microscope 1 a stripe pattern in the direction onto the tissue region 3 via the beam-splitter prism 15A with the aid of a controllable display 37, for example a digital mirror device (DMD) or an LCD display. In particular, the display 37 can be equipped with monochrome display illumination. Moreover, an illumination optical system 39 is arranged between the display 37 and the beam-splitter prism 15B and, in conjunction with the magnification changer 11 and the objective 5, it projects the stripe pattern into a plane, separated from the tissue region by the distance "d", such that an air image 41 of the grid displayed by means of the display 37 is generated in this plane, that is to say an image of the grid designed freely in the air.

A camera adaptor 19 with a camera 21 attached thereto is arranged on the interface 13B in the other partial beam path 9B, which camera is equipped with an electronic image sensor 23, for example a CCD sensor or a CMOS sensor. An electronic and, in particular, a digital image of the tissue region 3 can be recorded by means of the camera 21. If a stripe pattern is mirrored into the first partial beam path 9A in the direction onto the tissue region 3 via the interface 13A, the camera can also record the image of the air image 41 reflected by the tissue region 3.

Although there is only one camera 21 in the present exemplary embodiment, which camera is supplied a bundle of rays 25 coupled out of one of the two partial beam paths 9B, a further camera can also be arranged on the interface 13A and this second camera is supplied a bundle of rays coupled out of the other one of the two partial beam paths 9A in order to record an electronic and, in particular, a digital image of the tissue region 3. The second camera would allow the recording of stereoscopic images of the tissue region. In the operation microscope 1 illustrated in FIG. 1, the bundle of rays would then preferably be coupled out via the beam splitter 15A in the partial beam path 9A. If a display for mirroring in a stripe pattern into the partial beam path 9A in the direction onto the tissue region 3 is already arranged at this interface, a further beam splitter (not illustrated), for example a partly transparent mirror or a beam-splitter prism, would be arranged between the illumination optical system 39 and the beam-splitter prism 15A arranged in the partial beam path 9A.

A binocular tube 27 adjoins the interface 13 on the observer side. This tube has two tube objectives 29A, 29B, which focus the respective parallel bundle of rays 9A, 9B onto an intermediate image plane 31, that is to say, which image the observation image 3 on the respective intermediate image plane 31A, 31B. The intermediate images located in the intermediate image planes 31A, 31B are finally focused at infinity again by eyepiece lenses 35A, 35B and so an observer, for example a treating medical practitioner or an assistant, can observe the intermediate image with a relaxed eye. Moreover, there is an increase in the separation between the two partial bundles of rays 9A, 9B within the binocular tube by means of a mirror system or by means of prisms 33A, 33B in order to match said separation to the eye separation of the observer.

Moreover, the operation microscope 1 is equipped with an illumination device 43, which can be used to illuminate the tissue region 3 with broadband illumination light. For this, the illumination device 43 has a white-light source, for example a halogen incandescent lamp or a gas discharge lamp. In the present exemplary embodiment, the white-light source 45 is designed as a xenon lamp. The light emanating from the xenon lamp 45 is directed, via a deflection mirror 53, in the direction of the surface of the tissue region 3 in order to illuminate the latter. Additionally, an illumination optical system 55 is present in the illumination device and it ensures even illumination of the entire tissue region 3.

The illumination device 43 additionally comprises a filter wheel 47 with a narrowband spectral filter 49 that filters out one or more wavelengths from the illumination light of the xenon lamp 45. Herein, the spectral filter 49 in principle can be designed as a color filter or an interference filter (dichroic filter). In addition to the spectral filter 49, the filter wheel 47 moreover has a second filter section 51 that completely passes the light emitted by the xenon lamp 45, i.e. without filtering out a wavelength component. The filter wheel 47 is used to enable pulsed illumination of the tissue region 3 by measurement light when images of the tissue region 3 are recorded during a stimulation of the functional tissue areas, by means of which images the functional tissue areas can be located. The properties of the first spectral filter section 49 are in this case selected such that it filters out at least one wavelength of the light from the xenon lamp, at which wavelength stimulation leads to a change in at least one optical property of the reflected measurement light in the functional tissue areas. The method for locating the functional tissue areas in the tissue region 3 will be explained in more detail below with reference to FIG. 5.

Suitable wavelengths for the measurement illumination can vary depending on the effect to be measured. By way of example, stimulation of the functional tissue areas in the brain leads to the blood flow being increased in these areas in order to satisfy increased requirements for oxygen and glucose due to the stimulation. Furthermore, an increased concentration of hemoglobin leads to an increased proportion of oxygenated hemoglobin (oxyhemoglobin) in the veins running through the functional areas. In order to be able to locate functional areas on the basis of recorded images, it is therefore advantageous e.g. for the measurement illumination to comprise at least one wavelength at which the absorption of hemoglobin and oxyhemoglobin is very different. Such wavelengths in particular lie in the range between 400 and 500 nm, specifically at 415 nm, 436 nm and 473 nm. However, it is also possible to use wavelengths at which hemoglobin and oxyhemoglobin have equally strong absorption (so-called isosbestic points). Such wavelengths lie in the range between 400 and 600 nm, specifically at 422 nm, 452 nm, 500 nm, 530 nm, 546 nm, 579 nm and 584 nm. In particular, it is also possible to make use of combinations of wavelengths at which the absorption has the greatest difference and/or of wavelengths at which the absorption has the same strength. For this, the first filter section 49 has the corresponding transmission characteristic, or a plurality of filter wheels are connected in series, in which there is a filter section with the corresponding transmission characteristics for in each case at least one of the wavelengths.

Reference is made to the fact that the illumination beam path illustrated in FIG. 1 is very schematic and does not necessarily reproduce the actual profile of the illumination beam path. In principle, the illumination beam path can be designed as a so-called oblique illumination, which is the closest match to the schematic illustration of FIG. 1. In the case of such oblique illumination, the beam path runs at a relatively large angle to the optical axis of the objective 5 and, as illustrated in FIG. 1, can run completely outside of the objective. However, alternatively, it is also possible to let the illumination beam path of the oblique illumination pass through an edge region of the objective 5. A further possibility for arranging the illumination beam path is the so-called 0° illumination, in which the illumination beam path runs through the objective 5 and is coupled into the objective between the two partial beam paths 9A, 9B along the optical axis of the objective 5 in the direction onto the tissue region 3. Finally, it is also possible for the illumination beam path to be designed as so-called coaxial illumination, in which there is a first and a second partial illumination beam path. The partial beam paths are coupled into the microscope parallel to the beam paths 9A, 9B by one or more beam splitters and so the illumination runs coaxially with the two observation partial beam paths.

Figure 2:
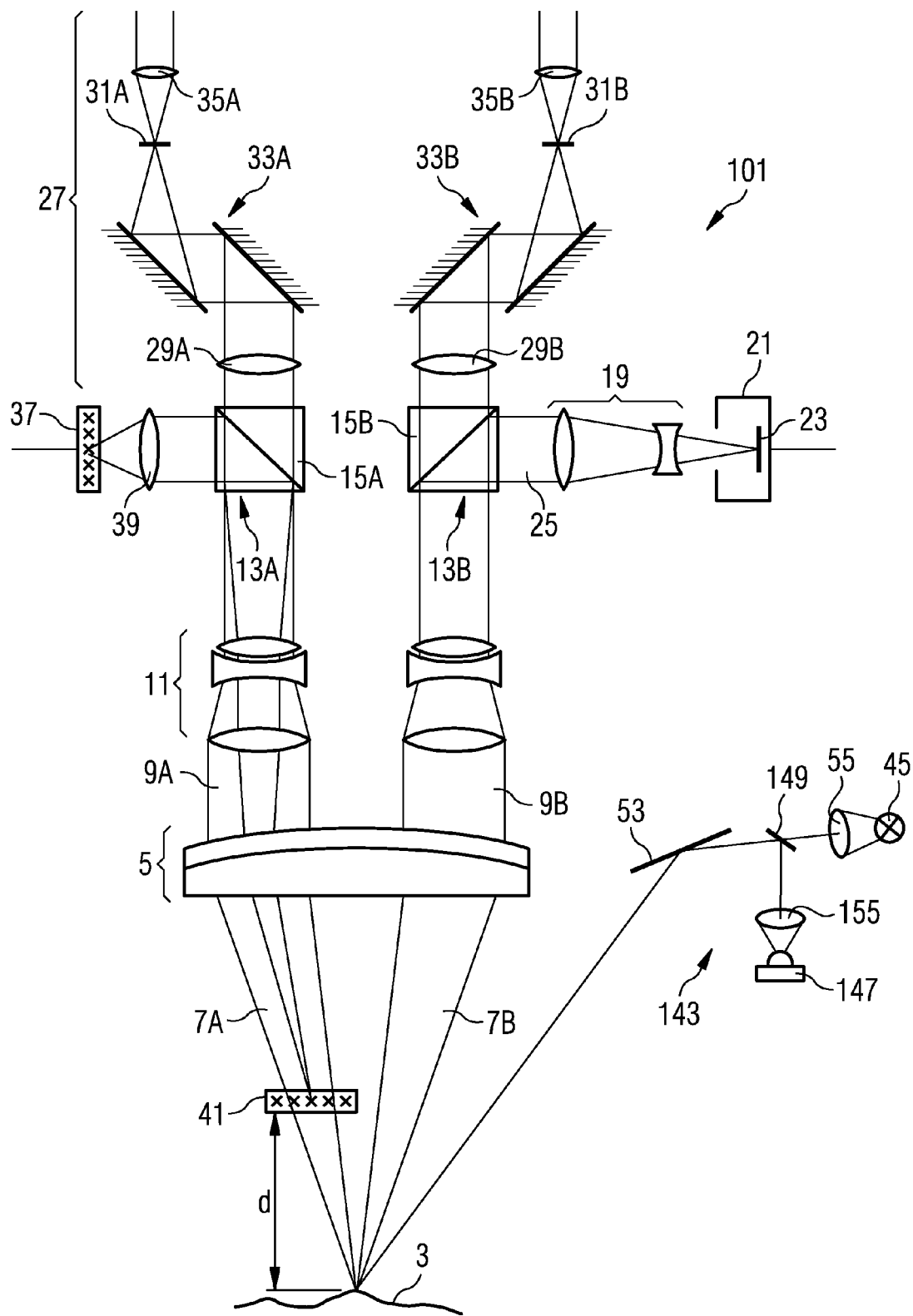
FIG. 2 shows a second exemplary embodiment of the device according to the invention.

A second exemplary embodiment of the invention is illustrated in FIG. 2. Elements of this exemplary embodiment corresponding to elements of the exemplary embodiment described with reference to FIG. 1 are denoted by the same reference signs as in FIG. 1 and are not explained again in order to avoid repetitions.

The exemplary embodiment illustrated in FIG. 2 differs from the exemplary embodiment illustrated in FIG. 1 only in its illumination device. The illumination device 43 of the second exemplary embodiment does not have a filter wheel. Instead of this, there is a narrowband light source 147 in addition to the white-light source 45, again embodied as a xenon lamp, and the light of said narrowband light source can be superposed on the beam path of the broadband illumination light emanating from the xenon lamp 45 by means of a beam splitter 149. The narrowband light source 147 can in particular be designed as a light-emitting diode or as an electroluminescent emitter, e.g. as an organic diode (OLED) or as an electroluminescent foil. It emits light at least one wavelength at which the stimulation of the functional tissue areas leads to a change in at least one optical property of the reflected measurement illumination in said tissue areas compared to the original measurement illumination. In particular, the measurement radiation emitted by the light-emitting diode 147 can have at least one wavelength discussed with reference to the first exemplary embodiment.

Moreover, an illumination optical system 155 is arranged between the light-emitting diode 147 and the beam splitter 149 and it ensures that during the illumination the tissue region 3 is completely and evenly illuminated by the measurement light.

Although a xenon lamp is present as broadband light source in the second exemplary embodiment, it is also possible that use is made of other gas discharge lamps or halogen incandescent lamps. Furthermore, there can be at least one further light-emitting diode in addition to the light-emitting diode 147, which further diode has a different emission wavelength as measurement illumination.

Figure 3:
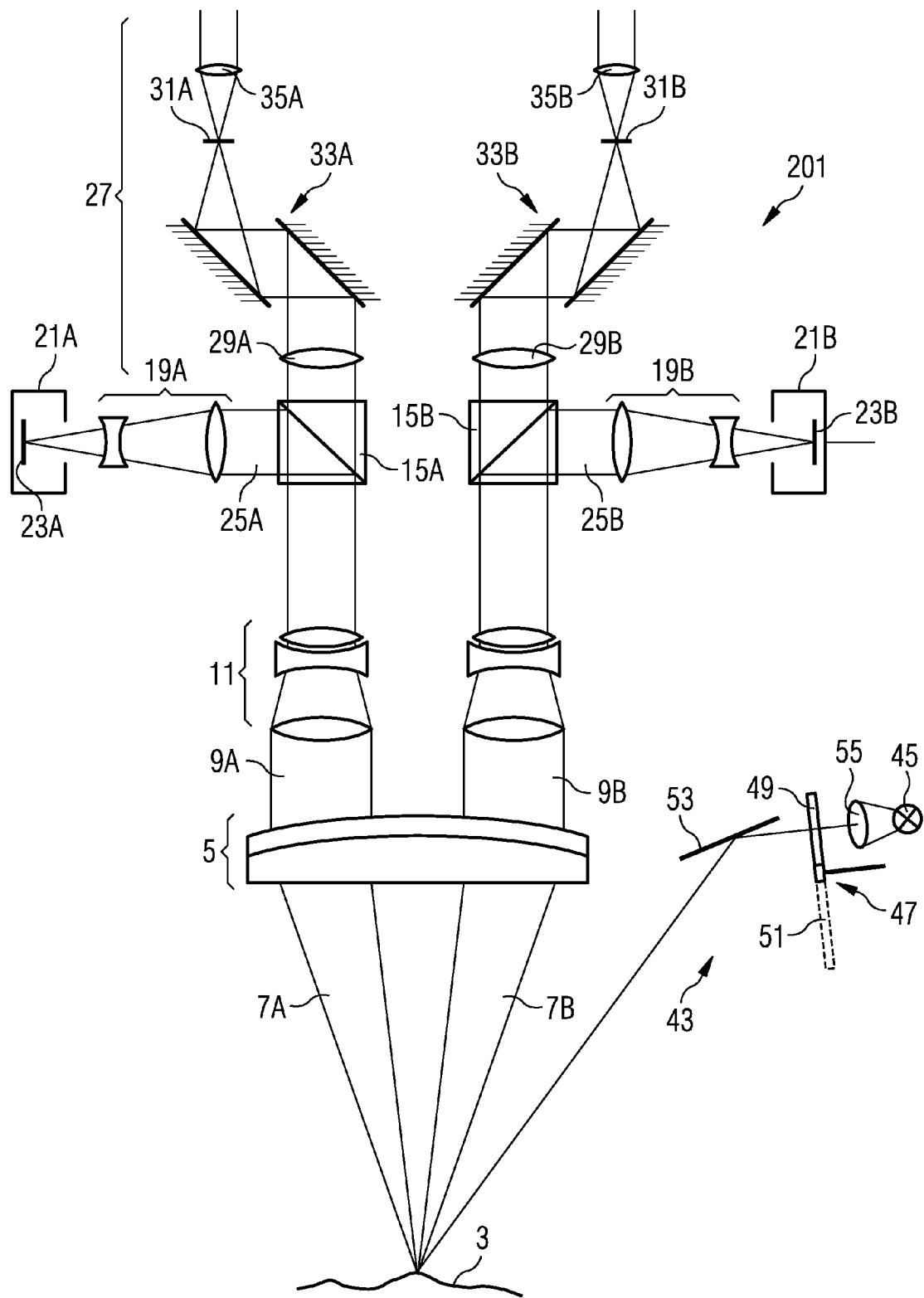
FIG. 3 shows a third exemplary embodiment of the device according to the invention.

A third exemplary embodiment of the invention is illustrated in FIG. 3. Elements that do not differ from elements of the first exemplary embodiment are denoted by the same reference signs as in FIG. 1 and are not explained again.

The operation microscope illustrated in FIG. 3 differs from the operation microscope illustrated in FIG. 1 in that there is no display with an illumination optical system arranged at the interface 13A. Therefore, this exemplary embodiment does not feature the generation of an air image at a distance "d" from the tissue region 3. Instead of the display, a camera 21A with an electronic image sensor 23A is arranged on the interface 13A by means of a camera adaptor 19A. A partial bundle of rays 25A is supplied to the electronic image sensor 23A, which bundle is coupled out of the stereoscopic partial bundle of rays 9A by means of the beam-splitter prism 15A. A stereoscopic image of the tissue region 3 can be generated by means of the two cameras 21A, 21B, and the topography of the tissue region 3 can be determined from the image by means of photogrammetry.

Although the exemplary embodiment illustrated in FIG. 3 has been illustrated with an illumination device as per the first exemplary embodiment, it can instead also be equipped with an illumination device as per the second exemplary embodiment.

In a further exemplary embodiment of the device according to the invention illustrated in FIG. 4, the air image of a stripe pattern is generated via the illumination beam path rather than via an observation beam path. In contrast to FIGS. 1 to 3, FIG. 4 only shows the illumination device 243 and the objective 5 of the operation microscope. Here, the elements not illustrated in principle can correspond to those in one of the exemplary embodiments illustrated in FIGS. 1 to 3.

In respect of the light-emitting diode 147 and the white-light source 45, as well as the associated illumination optical systems 55, 155 and the beam splitter 149, the illumination device corresponds to the corresponding elements of the exemplary embodiment illustrated in FIG. 2. However, in contrast to the illumination device of the second exemplary embodiment, the illumination device of the fourth exemplary embodiment comprises a display 237, which in particular can be designed as a monochrome LCD display, and an illumination optical system 239, with the aid of which an air image 241 of the stripe pattern illustrated on the display 237 is generated at the distance "d" from the tissue region 3. The bundle of rays emanating from the illumination optical system 239 is coupled into the illumination beam path via a beam splitter 245, for example a partly transparent mirror or a beam-splitter prism. This refinement of the illumination optical system can be used, in particular, in conjunction with an oblique illumination or a 0° illumination. The refinement described with reference to FIG. 5 is advantageous, particularly when the interface 13 should be put to a different use, for example in order to record stereoscopic images with the aid of two cameras or to input data for the treating medical practitioner.

The operation of the device according to the invention for locating functional tissue areas in a tissue region will be explained in the following text with reference to FIG. 5. This figure shows a functional block diagram of the device according to the invention, on the basis of which a possible procedure of the method according to the invention for locating functional tissue areas in a tissue region is explained.

The block diagram is based on the exemplary embodiment of the device according to the invention illustrated in FIG. 2 and shows, inter alia, the display 37, the light-emitting diode 147 and the camera chip 23. Connected to the display is a pattern generator 301, which generates a stripe pattern to be displayed on the display 37, the light-emitting diode 147 is connected to a modulator 303, which brings about a pulsed emission of the measurement light, and the electronic image sensor 23 is connected to camera electronics 305, which read out the electronic image sensor 23 and furthermore allow the sensitivity of the pixels in the electronic image sensor 23 to be set.

The pattern generator 301, the modulator 303 and the camera electronics 305 are connected to a trigger 307. The latter serves to synchronize the generation of the stripe pattern, the emission of measurement light pulses and the readout of the electronic image sensor 23. Thus, it is possible to design the readout frequency of the electronic image sensor to have an integer multiple of a basic frequency. By way of example, if the readout rate is double the basic frequency, it is possible to set the pulse frequency of the pulsed measurement illumination to the basic frequency and so the electronic image sensor 23 respectively alternately records an image of the tissue region with measurement illumination and an image of the tissue region without measurement illumination. Should the readout rate of the electronic image sensor 23 correspond to three times the basic frequency, and the display is likewise operated in a pulsed fashion at the basic frequency, with there being a phase shift of one period of the basic frequency between the pulsed operation of the display 37 and the pulsed operation of the light-emitting diode 147, it is possible to use the electronic image sensor to record image sequences in which an image of the reflected stripe pattern is followed by an image with measurement light, which in turn is followed by an image without measurement light. It is understood that it is also possible to match the recording sequence to the respective specifications or requirements in a targeted fashion by a suitable selection of the frequencies. Thus, it is not mandatory for an image of the reflected stripe pattern to be recorded in each period in order to determine the topography of the tissue region therefrom. In principle, in order to determine the topography, it suffices if images of the stripe pattern with stripes extending in a first direction and images of the stripe pattern with stripes extending in a second direction are measured at the beginning of the measurement. However, it is also possible for the tissue region to move during the stimulation or for the topography to change during the stimulation, for example because tissue regions or blood vessels expand or contract. Therefore, it can be advantageous for the determination of the topography, i.e. the recording of reflected stripe patterns as well, to be carried out repeatedly. This affords the possibility of taking into account changes in position and/or changes in topography when locating the functional tissue areas.

In order to locate the functional tissue areas from an image with measurement illumination and an image without measurement illumination, the device illustrated in FIG. 5 has a topography determination unit 309, a correction unit 311, a difference-forming unit 313, a storage 315, an evaluation unit 317 and a buffer 319.

The topography acquisition unit 309 is connected to the camera electronics 305 for receiving electronic images. It is designed for determining the topography of the tissue region 3 from images of the stripe pattern. For this, use can be made of a so-called phase-shift method, as is known from US 2008/0317334 A1. By way of example, in such a method, use is made of a first series of four stripe patterns, wherein all stripe patterns have the same spatial modulation but have a phase that is shifted in each case by 90° with respect to one another. During the reflection from an uneven object such as the tissue region 3, the phases of the spatial stripe pattern are locally influenced by the topography of the object. The topography acquisition unit 309 then locally evaluates the phases of the reflected stripe pattern and the difference with respect to the original phase of the non-reflected stripe pattern is determined in a spatially resolved fashion. This method is repeated with a second sequence of stripe patterns, in which the direction of extent of the stripes is rotated compared to the first sequence (it is advantageously rotated by 90°). The local inclines determined thereby are then used by the topography determination unit 309 for assembling the topography of the tissue region. Reference is made to US 2008/0317334 A1 for details of the method.

If, as described above, there is a recording sequence of the type "recording a reflected stripe projection, recording an image with measurement light, recording an image without measurement light", one image of a stripe pattern of a stripe pattern sequence can be recorded in each sequence. The topography can then be determined after eight periods of the basic frequency.

Like the topography determination unit 309, the difference-forming unit 313 is connected to the camera electronics 305 for receiving electronic images. Moreover, the difference-forming unit 313 is connected to a buffer 319, which is likewise connected to the camera electronics 305 for receiving electronic images. The buffer 319 serves to buffer an image with measurement illumination until the subsequent image without measurement illumination has been recorded. It is understood that, alternatively, it is also possible to buffer an image without measurement illumination until an image with measurement illumination has been recorded. The difference-forming unit 313 forms a difference image from the image received from the camera electronics 305 and the image buffered in the buffer 319 in order to eliminate, as far as possible, the surrounding light effects contained in both images in the same fashion.

The correction unit 311 is connected to the topography determination unit 309 for receiving the determined topography data and to the difference-forming unit 311 for receiving the difference image. It is used to correct the difference image on the basis of the determined topography data such that undefined radiation and scatter angles are defined as far as possible. Moreover, the storage 315 is connected to the correction unit 311 for receiving a corrected difference image. The storage 315 is used to store a corrected difference image of the tissue region 3, which image was recorded without stimulation of the functional tissue areas.

The evaluation unit 317 is connected to both the correction unit 311 for receiving a corrected difference image recorded during the stimulation, and to the storage 315 for receiving the difference image obtained without the stimulation. In the evaluation unit 317, there is a comparison between the corrected difference image obtained during the stimulation and the corrected difference image obtained without stimulation in order to locate the functional tissue areas on the basis of the comparison. In the simplest case, the comparison can be implemented by forming a difference. The result of the comparison is then output as a data record or as an image of the functional tissue areas.

The entire device illustrated in FIG. 5 is controlled by a control unit 321, which is connected to all other units for outputting control signals. From the control unit 321, the pattern generator receives the information relating to the pattern to be generated, the modulator receives the information about the pulse frequency of the illumination to be set, and the camera electronics 305 receive the information relating to the readout frequency. The topography determination unit 309 is controlled to the effect that it determines the topography determination only on the basis of images of reflected stripe patterns. In respect of the buffer 319 and the difference-forming unit 313, the control apparatus 321 controls the overwriting of the buffer 319, and the readout of the buffer 319 and of the camera electronics 305 by the difference-forming unit 313. Likewise, it controls the readout of the topography data from the topography-averaging unit 309, the readout of the difference images from the difference-forming unit 313 by the correction unit 311, the readout of the corrected difference image without stimulation from the storage 315 and the readout of the corrected difference image with stimulation from the correction unit 311.

Moreover, the control unit 321 can also control the stimulation, in particular such that the latter is pulsed with a stimulation pulse frequency. By way of example, stimulation phases and phases without stimulation can alternate successively a number of times and take approximately 30 seconds, but last at least so long that the effect to be measured can be set up or the effect to be measured can decay. Since the dynamics of set up and decay lie, for example, in the range of between one second and ten seconds, the stimulation phases and the phases without stimulation each take longer than one second, preferably longer than ten seconds. In order to achieve sufficient integration times, measurements are typically taken over a longer period of time. The pulse frequency of the measurement illumination can then be controlled such that it is a large integer multiple of the stimulation pulse frequency and that the same number of images are taken in each case during a stimulation phase and during a phase without stimulation.

Although the determination of the topography was described on the basis of a deflectometric method in respect of the block diagram illustrated in FIG. 5, the topography can alternatively be determined on the basis of a plurality of other methods. If the device according to the invention is designed as per the exemplary embodiment illustrated in FIG. 3, photogrammetric methods, in particular, should be considered. In this case, the topography acquisition unit would also be connected to corresponding camera electronics of the second camera in addition to the camera electronics 305 of the camera 23 and so it can receive two stereoscopic partial images. However, in principle, the topography determination unit can also be based on, for example, so-called shape shading, in which images of the tissue region 3 are recorded, with the illumination coming from different directions. The topography can then be inferred from the shadows due to the illumination. In principle, so-called time-of-flight methods, triangulation methods and pattern-projection methods, in which a stripe pattern is directly projected onto the surface of the tissue area instead of producing an air image, are also possible for determining the topography of the tissue region 3.

In a development of the device illustrated in FIG. 5, the topography acquisition unit 309 is moreover designed to determine those zones in the tissue region 3 in which total reflection occurs in a spatially resolved fashion on the basis of the reflected stripe pattern. In this refinement, the information relating to those locations at which total reflection is determined is output to the control unit 321, which then controls the camera electronics 305 on the basis of the received data such that there is a reduction in the sensitivity of the pixel regions of the image sensor 23 in which zones with total reflection are imaged, in particular below the saturation limit. This masks zones of the tissue region 3, which due to total reflection merely contain light reflected from the film of moisture, i.e. which contain no useful signal, in the recorded image in order to avoid disturbing reflections. This then allows the location of functional tissue areas at least in those zones in which a useful signal can be measured.

Although use is made in FIG. 5 of a light-emitting diode 147 for generating the measurement light, use can also be made of a broadband light source for generating the measurement light, as illustrated in FIG. 1. In FIG. 5, the light-emitting diode 147 should then be replaced by a filter 49, which can periodically be introduced into the beam path, and the modulator 303 should be replaced by a frequency generator. Use can be made in particular of the filter illustrated in FIG. 1 and arranged on a filter wheel 47. However, such a filter 49 can also be arranged on an oscillating support rather than on a filter wheel 47 in order to generate the measurement light pulses. If use is made of a filter 49 as described with reference to FIG. 1, the filter 49 is introduced into the beam path when the measurement light should be masked from the illumination. In order to generate the measurement light pulses, the filter 49 is then removed from the beam path and so the tissue region is illuminated by both the broadband light and the measurement light. Here, the pulse frequency can be set via the rotational frequency of the filter wheel 47, or, if an oscillating filter is used, by means of the oscillation frequency.

In addition to the described deviations from the exemplary embodiments, further deviations from the exemplary embodiments are possible. Thus, for example, it is possible that use is made of either monochromatic light or white light for illuminating the tissue region for carrying out the deflectometric method, wherein, in the case of white light, a narrowband filter is arranged in front of the camera 21 and said filter only allows a component of the white light to pass. However, in principle it is also possible to carry out the deflectometric measurement at the same time in a plurality of wavelength ranges. This can be brought about by the stripe projection being brought about by a plurality of mutually separate wavelengths or by a filter device allowing a plurality of wavelengths to pass being arranged in front of the camera 21. Moreover, if there should not be a correction of the difference images on the basis of topography data, the topography determination unit 309 and the correction unit 311 can be dispensed with and the difference-forming unit 313 can be connected directly to the readout unit 317 and the storage 315. If, on the other hand, there should merely be correction on the basis of the topography data but no elimination of surrounding light influences, the buffer 319 and the difference-forming unit 313 can be dispensed with. The correction unit 311 would then be connected directly to the electronic image sensor 23.

The invention claimed is:

1. A method for locating functional tissue areas in a tissue region, the method comprising the steps of:
    illuminating the tissue region by providing a measurement illumination with at least one wavelength at which a stimulation of the functional tissue areas leads to a change in at least one optical property of a reflected measurement illumination as compared to the measurement illumination;
    recording at least one image of the tissue region without stimulation while the tissue region is illuminated with the measurement illumination;
    recording at least one image of the tissue region without stimulation while the tissue region is not illuminated with the measurement illumination;
    forming a comparison image of the tissue region from the difference of the at least one image of the tissue region recorded without stimulation while the tissue region is illuminated with the measurement illumination and the at least one image of the tissue region recorded without stimulation while the tissue region is not illuminated with the measurement illumination, thereby eliminating or reducing influences of surroundings from the comparison image;
    recording at least one image of the tissue region during stimulation while the tissue region is illuminated with the measurement illumination;
    recording at least one image of the tissue region during stimulation while the tissue region is not illuminated with the measurement illumination;
    forming a stimulation image of the tissue region from a difference between
    a) the at least one image of the tissue region recorded during stimulation while the tissue region is illuminated with the measurement illumination, and
    b) the at least one image of the tissue region recorded during stimulation while the tissue region is not illuminated with measurement illumination, thereby eliminating or reducing influences of the surroundings from the stimulation image; and
    locating the functional tissue areas in the tissue region on the basis of the change in the at least one optical property of the reflected measurement illumination as compared to the original measurement illumination by determining a difference between the stimulation image of the tissue region and the comparison image of the tissue region.

2. The method of claim 1, wherein the step of illuminating the tissue region with a measurement illumination comprises applying a pulsed measurement illumination of the tissue region, images of the tissue region with measurement illumination are recorded during the measurement illumination pulses, and images of the tissue region without measurement illumination are recorded between the measurement illumination pulses.

3. The method of claim 2, wherein the images are recorded with a recording frequency that is an integer multiple of the pulse frequency of the measurement illumination.

4. The method of claim 3, wherein the tissue region is stimulated by applying a pulsed stimulation with a stimulation pulse frequency and the pulse frequency of the measurement illumination is a large integer multiple of the stimulation pulse frequency.

5. The method of claim 1, further comprising:
    applying continuous illumination of the tissue region with broadband illumination light,
    and wherein the step of recording the image of the tissue region without stimulation and without measurement illumination is carried out with the continuous illumination of the tissue region.

6. The method of claim 5, further comprising using a filter to generate the measurement illumination, the filter being operative to filter the at least one wavelength of the measurement illumination out of the broadband illumination light.

7. The method of claim 5, further comprising using a measurement light source with the at least one wavelength of the measurement illumination in addition to the continuous illumination in order to generate the measurement illumination.

8. The method of claim 1, wherein the measurement illumination comprises a first wavelength, at which the stimulation in the functional tissue regions leads to a change in at least one optical property of the reflected measurement illumination, and at least one second wavelength, at which the stimulation in the functional tissue regions leads to a change in at least one optical property of the reflected measurement illumination.

9. The method of claim 8, further comprising simultaneously measuring illumination by the first wavelength and the at least one second wavelength.

10. The method of claim 8, further comprising successively measuring illumination by the first wavelength and measurement illumination by the at least one second wavelength during the measurement illumination.

11. A method for locating functional tissue areas in a tissue region, the method comprising the steps of:
   illuminating the tissue region by providing a measurement illumination with at least one wavelength at which a stimulation of the functional tissue areas leads to a change in at least one optical property of a reflected measurement illumination as compared to the measurement illumination;
   determining a topography of the tissue region;
   recording at least one image of the tissue region without the stimulation;
   forming a comparison image of the tissue region by correcting the at least one image recorded without stimulation on the basis of the topography;
   recording at least one image of the tissue region during the stimulation;
   forming a stimulation image of the tissue region by correcting the at least one image recorded during stimulation on the basis of the topography; and
   locating the functional tissue areas on the basis of a change in the at least one optical property of the reflected measurement illumination as compared to the measurement illumination by determining the difference between the at least one image of the tissue region obtained during the stimulation and the at least one image of the tissue region obtained without stimulation.

12. The method of claim 11, further comprising evaluating a pattern reflected by the tissue region in the recorded images in order to determine the topography.

13. The method of claim 12, wherein the determined topography is used to determine those zones of the tissue region in which total reflection is to be expected due to a film of moisture present on the tissue region.

14. The method of claim 13, further comprising reducing the sensitivity of the recording in those zones of the tissue region in which total reflection is expected.

15. The method of claim 11, wherein the step of determining the topography is carried out by a pattern-projection method, a triangulation method, a photogrammetric method, a time-of-flight method or a shape-shading method.

16. The method of claim 11, further comprising generating a topographic map of the tissue region.

17. A device for locating functional tissue areas in a tissue region (3), comprising:
   a measurement illumination device (45, 49, 147) for generating measurement illumination comprising at least one wavelength at which stimulation of the functional tissue areas leads to at least one change in at least one optical property of the reflected measurement illumination;
   an electronic image sensor (23) for recording images of the tissue region (3), and
   a control apparatus (321) connected to the electronic image sensor (23), the control apparatus controlling the electronic image sensor such that, during a time period without stimulation, the electronic image sensor respectively records at least one image of the tissue region (3) while the tissue region (3) is illuminated with the measurement illumination and at least one image of the tissue region (3) while the tissue region is not illuminated with the measurement illumination and, during the stimulation, the electronic image sensor records at least one image of the tissue region (3) while the tissue region is illuminated with the measurement illumination and at least one image of the tissue region (3) while the tissue region is not illuminated with the measurement illumination;
   a difference image generator (313) connected to the electronic image sensor (23) for receiving the recorded images, the difference image generator determining a stimulation image from a difference between:
   at least one image recorded during the stimulation while the tissue region is illuminated with the measurement illumination, and
   at least one image recorded during the stimulation while the tissue region is not illuminated with the measurement illumination, thereby eliminating or reducing influences of the surroundings from the stimulation image, the difference image generator further determining a comparison image from a difference between:
   at least one image recorded without the stimulation while the tissue region is illuminated with the measurement illumination, and
   at least one image recorded without stimulation while the tissue region is not illuminated with the measurement illumination, thereby eliminating or reducing influences of surroundings from the comparison image; and
   an evaluation unit (317) connected to the difference image generator (313) for receiving the stimulation image and the comparison image determined by the difference image generator (313) and locating the functional tissue areas by determining a difference between the stimulation image and the comparison image.

18. The device of claim 17, wherein
   the measurement illumination device (45, 49, 147) is designed to generate a pulsed measurement illumination,
   the control apparatus (321) connected to the electronic image sensor (23) controls the electronic image sensor (23) such that the electronic image sensor (23) records images of the tissue region (3) during the measurement illumination pulses and records images between the measurement illumination pulses.

19. The device of claim 17, further comprising an illumination device (45) for continuous illumination of the tissue region (3) with broadband illumination light.

20. The device of claim 19, wherein the measurement illumination device (45, 49) is formed by the illumination device (45) for the continuous illumination and a filter (49), which can be brought into the illumination beam path of the illumination device (45) and filters out the at least one wavelength of the measurement illumination from the broadband illumination light.

21. The device of claim 19, wherein the measurement illumination device (147) is present in addition to the illumination device (45) for the continuous illumination.

22. The device of claim 17, wherein the measurement illumination device emits a first wavelength, at which the stimulation in the functional tissue areas leads to a change in the at least one optical property of the reflected measurement illumination, and at least one second wavelength, at which the stimulation in the functional tissue areas leads to a change in the at least one optical property of the reflected measurement illumination.

23. The device of claim 22, further comprising a measurement illumination control apparatus, which allows a pulsed operation of the measurement illumination device such that measurement illumination pulses at the first wavelength and measurement illumination pulses at the second wavelength are emitted in succession.

24. The device of claim 17, wherein the device is an operation microscope with optics for focusing an image.

25. A device for locating functional tissue areas in a tissue region, comprising:
- a measurement illumination device (45, 49, 147) for generating measurement illumination comprising at least one wavelength at which the stimulation of the functional tissue areas therein leads to at least one change in at least one optical property of the reflected measurement illumination,
- an electronic image sensor (23) for recording images of the tissue region (3),
- a topography acquisition unit (37, 237, 301, 309), which determines topography data of the tissue region (3),
- a correction unit (311), which is connected to the electronic image sensor (23) for receiving the images and to the topography acquisition unit (37, 237, 301, 309) for receiving the topography data and which is designed to determine a stimulation image from an image recorded during stimulation by correcting the image on the basis of the determined topography data, and to determine a comparison image from an image recorded during a time period without stimulation on the basis of the determined topography data;
- an evaluation unit which is connected to the correction unit for receiving the stimulation image and the comparison image and which is designed to locate the functional tissue areas by determining a difference between the stimulation image and the comparison image.

26. The device of claim 25, characterized in that wherein the topography acquisition unit (37, 237, 301, 309) comprises a pattern-projection unit (37, 237), a triangulation unit, a photogrammetric unit, a shape-shading unit or a time-of-flight unit.

27. The device of claim 26, wherein the topography acquisition unit (37, 237, 301, 309) comprises a pattern generator (301) for generating a pattern to be reflected by the tissue region (3) and a deflectometry unit (309) for determining the tomography data from the reflected pattern.

28. The device of claim 27, further comprising a total-reflection determination unit integrated in or connected to the topography acquisition unit (37, 237, 301, 309) for receiving the topography data, the total-reflection determination unit being designed to determine those zones of the tissue region (3) in which total reflection occurs due to a film of moisture present on the tissue region (3) on the basis of the topography data and output corresponding total-reflection data.

29. The device of claim 28, further comprising an adjustment unit (321) connected to the electronic image sensor (23) for acting on the light-sensitivity thereof and to the total-reflection determination unit for receiving the total-reflection data, which adjustment unit is designed to reduce the light sensitivity of the electronic image sensor (23) in pixel areas, in which tissue region sections with total reflection are imaged, when recording the images recorded with the measurement illumination.

* * * * *